US009706936B2

(12) United States Patent
Hannemann et al.

(10) Patent No.: US 9,706,936 B2
(45) Date of Patent: Jul. 18, 2017

(54) SENSOR INSTRUMENT

(71) Applicant: Siemens Aktiengesellschaft, Munich (DE)

(72) Inventors: Thilo Hannemann, Erlangen (DE); Andre Henning, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 228 days.

(21) Appl. No.: 14/546,230

(22) Filed: Nov. 18, 2014

(65) Prior Publication Data
US 2015/0141790 A1 May 21, 2015

(30) Foreign Application Priority Data
Nov. 18, 2013 (DE) .................. 10 2013 223 465

(51) Int. Cl.
*A61B 5/0404* (2006.01)
*A61B 5/0408* (2006.01)
*A61B 5/00* (2006.01)

(52) U.S. Cl.
CPC ........ *A61B 5/04082* (2013.01); *A61B 5/0404* (2013.01); *A61B 5/04085* (2013.01); *A61B 5/6834* (2013.01); *A61B 5/0006* (2013.01); *A61B 2560/0468* (2013.01)

(58) Field of Classification Search
CPC .............. A61B 5/0404; A61B 5/04082; A61B 5/04085; A61B 5/6834
USPC ....................................................... 600/387
See application file for complete search history.

(56) References Cited

U.S. PATENT DOCUMENTS

| 2,580,628 | A | * | 1/1952 | Welsh | A61B 5/04082 439/41 |
| 3,490,442 | A | * | 1/1970 | Streu | A61B 5/04082 600/384 |
| 3,795,241 | A | * | 3/1974 | Golovko | A61B 5/0408 600/391 |
| 3,848,582 | A | * | 11/1974 | Milani | A61B 5/044 600/372 |
| 3,862,627 | A | * | 1/1975 | Hans, Sr. | A61B 5/04082 600/387 |
| 3,976,055 | A | * | 8/1976 | Monter | A61B 5/04082 252/503 |
| 4,369,793 | A | * | 1/1983 | Staver | A61B 5/04082 600/387 |
| 4,432,367 | A | | 2/1984 | Piesinger | |
| 4,448,199 | A | * | 5/1984 | Schmid | A61B 5/02438 600/393 |

(Continued)

FOREIGN PATENT DOCUMENTS

| CN | 201088583 Y | 7/2008 |
| CN | 201542632 U | 8/2010 |

(Continued)

OTHER PUBLICATIONS

Translation of DE2742058.*

*Primary Examiner* — Lee S Cohen
(74) *Attorney, Agent, or Firm* — Schiff Hardin LLP

(57) ABSTRACT

A sensor instrument for generation of electrocardiograms, in particular for cardiac computed tomography, has two electrodes, an electronic module and a support, wherein multiple suction elements for affixing the support to the body of a subject (are positioned on the support.

12 Claims, 3 Drawing Sheets

(56) References Cited

U.S. PATENT DOCUMENTS

| | | | | |
|---|---|---|---|---|
| 4,469,105 A | * | 9/1984 | Staver | A61B 5/04082 |
| | | | | 600/387 |
| 4,535,783 A | * | 8/1985 | Marangoni | A61B 5/0404 |
| | | | | 600/382 |
| 4,852,574 A | * | 8/1989 | Inoue | A61B 5/04082 |
| | | | | 600/387 |
| 5,345,935 A | * | 9/1994 | Hirsch | A61B 5/4362 |
| | | | | 600/376 |
| 6,185,442 B1 | | 2/2001 | Samson | |
| 8,473,040 B2 | * | 6/2013 | Paul | A61B 5/0404 |
| | | | | 600/508 |
| 2009/0022941 A1 | | 1/2009 | Fischer et al. | |
| 2012/0310053 A1 | | 12/2012 | Henning et al. | |
| 2014/0309514 A1 | | 10/2014 | Zhou et al. | |

FOREIGN PATENT DOCUMENTS

| | | |
|---|---|---|
| CN | 201691918 U | 1/2011 |
| CN | 203089113 U | 7/2013 |
| DE | 2742058 * | 3/1979 |
| RU | 2006204 C1 | 1/1994 |

\* cited by examiner

SENSOR INSTRUMENT

BACKGROUND OF THE INVENTION

Field of the Invention

The invention concerns a sensor instrument for generation of electrocardiograms, in particular for cardiac computed tomography.

Description of the Prior Art

Measurement devices or sensor instruments that serve to detect and record the electrical activities of heart muscle fibers of humans or animals are widespread and are used in a variety of fields of application.

For example, relatively simple embodiments are known that are merely designed to determine a heart rate, and used, for example, for monitoring purposes during an athletic activity, and are designed in the manner of a wristwatch or a chest belt, for example.

Measurement devices or sensor instruments that are provided for the medical field are thereby of particular importance. These are often designated as EKG devices and normally have a much higher degree of complexity, which typically also results in a more complicated handling of such a device. However, elaborate and time-intensive handling is undesirable in principle since an efficient workflow in a normal clinical operation is hereby impeded. In contrast to this, in the field of emergency medicine a high time expenditure due to a complicated handling is not only undesirable but can be significantly problematic since, as is known; the time factor plays a decisive role in emergency situations.

In addition, in the medical field there is the problem that measurement devices or sensor instruments are often used simultaneously with different medical apparatuses, such that a high degree of compatibility is required for multiple measurement devices or sensor instruments in the medical field so that the different devices and apparatuses do not mutually interfere. For example, it is known to use an EKG apparatus in order to essentially "trigger" a computed tomography image during cardiac computed tomography. By means of the EKG apparatus, time segments are determined in which the heart of a patient to be examined executes only slight movements or no movements in order to then generate measurement data for a graphical depiction of the heart in precisely these time segments. Since the electromagnetic radiation of the computed tomography apparatus tends to be problematic for electronic components, an EKG apparatus is used that has electronic components accommodated in a housing that can be positioned outside of the radiation region of the computed tomography apparatus, and for example this housing is placed at the foot of the patient bed of the computed tomography apparatus. Only the electrodes of the EKG apparatus, which are usually designed as adhesive electrodes and are attached to the body of the patient in order to establish a galvanically conductive contact, are then located in the radiation region. For the generation of an electrocardiogram, at least two electrodes are thereby necessary that are firmly adhered to the body of the patient independently of one another (thus with a spatial separation from one another) and are connected by wires. In practice, metallic elements that interfere with the computed tomography image data generation and often cause image artifacts are often located at the electrodes themselves, such interference is, however, generally accepted.

SUMMARY OF THE INVENTION

An object of the invention is to provide an advantageous sensor instrument for generation of electrocardiograms.

A sensor instrument in accordance with the invention serves to generate electrocardiograms and is in particular designed for cardiac computed tomography. Such a sensor instrument has two electrodes, an electronic module and a support, with multiple suction elements positioned on the support to affix the support to a body of a patient.

The term "electrocardiogram" as used herein encompasses not only electrocardiograms in the specific cardiac medicine sense, but also all data and signals that characterize the electrical activities of heart muscle fibers of humans or animals, or that characterize a current state of a heart.

The sensor instrument in accordance with the invention is designed for particularly simple handling, such that it is ready for use with a few simple hand movements (and accordingly very quickly), so the sensor instrument is particularly suitable for emergency medicine.

The term "suction elements" as used herein encompasses elements that can be attached to a surface by the generation of a negative pressure in a closed (airtight) volume and can be released again from the surface by canceling the negative pressure. Suction cups are preferably used as such suction elements, the suction cups being made of a flexible and biocompatible material (for example silicone) and also being suitable for frequent cleaning, in particular with common disinfection agents.

The electrodes of the sensor element are additionally preferably all attached to the support in order to cause all electrodes of the sensor element to also be positioned with the support on the body of the respective patient. The electrodes of the sensor element are thus no longer positioned and attached individually to the body of the respective patient, as is conventional. Instead, a simultaneous positioning and attachment of all electrodes to the body of the respective patient preferably takes place with the use of the support, so a significant time savings is achieved.

The support preferably has a handhold (grip) or handle that is ergonomically designed. This enables an operator—in particular a physician or a first responder—to grip the handhold with one hand and to subsequently hold and direct the support by manipulation of the handhold.

In an embodiment, the support itself is designed in the form of a handhold so that an additional handhold can be omitted. In both cases, the support can be held and directed securely, so accidentally letting the support fall or slide out of the hand is unlikely. The support is fashioned overall in the form of a housing in which different modules (components) of the sensor instrument are appropriately accommodated.

In the embodiment in which the support itself is fashioned in the manner of a handhold, the support is preferably designed with a curved shape, with two support ends at each of which a suction element is respectively positioned. In this case, the sensor instrument thus has exactly two suction elements.

To adapt to various anatomies of different patients, it is additionally advantageous for the suction elements to be attached to the support so as to be movable, in particular pivotable. An appropriate mobility thus is achieved in an embodiment wherein, for example, each suction element is connected with the support via a ball joint. Alternatively, the desired alignment capability or adaptation capability of the suction elements—and thus a certain relative movement of the suction elements relative to one another—can be achieved by the suction elements or the supports being made from a suitable (and thus flexible) material.

In the embodiment of the support as a handhold, it is additionally advantageous for a movement in the direction of a longitudinal axis of the support to be permitted via the movable attachment or flexible embodiment, in contrast to which a movement in the direction of a transverse axis orthogonal to the longitudinal direction is hindered. The goal is for the support to stand out essentially vertically from the body of the patient after the positioning on and attachment to the body of the respective patient, and for the support to not just lie on the body. Only the suction elements, and possibly the electrodes, should be in direct contact with the body of the respective patient and contact the body.

For additional variability, the support is preferably designed such that the distance between the suction elements is movable and thus is adjustable. For this purpose, the support can preferably be extended. For example, if the support is designed as an arc-shaped handhold, it (for example) has a straight, cylindrical middle part which is designed telescopically so that the length of the support can be modified and adjusted by extending the telescoping middle part. In this way, larger anatomical differences—for example as exist between adults and children—can be taken into account. Alternatively, the different, and in particular anatomically dependent, requirements are taken into account by multiple supports of different design, in particular of different sizes, are manufactured, thus for example one version for adults and one version for children.

Furthermore, it is advantageous for the sensor instrument to include a trigger element with which multiple (in particular all) suction elements can be activated and thus can be attached to the body of the respective patient. Such a trigger element can be designed in the manner of a pressure plate or a button, for example. In this way, the number of hand motions or movements that are necessary in order to make the sensor instrument ready for use can be further reduced, so the handling is even more simplified and even less time-intensive.

In the embodiment of the support as a handhold, it is additionally preferable to position the trigger element in the region of the handhold so that the trigger element either triggered by a firm grip on the handhold itself or can be comfortably reached and operated with the thumb after gripping the handhold. This ultimately means that, for positioning and attachment of the support, in this case only the support designed in the manner of a handhold must be gripped with one hand and be directed to the body of the patient, and attachment to the body of the respective patient then takes place via a hand movement or thumb movement of the hand holding the handhold. As a result, a support (and ultimately also a sensor instrument) is provided that is designed for one-handed handling and accordingly can be operated with only one hand.

In another embodiment of the sensor instrument, suction elements are activated purely mechanically by at least one bellows and are affixed to the body of the respective patient as a result. The sensor instrument can thus be executed particularly simply, which benefits it useful life. Alternatively, the negative pressure with which the suction elements are held on the body of a respective patient in the activated state can be generated by an electric pump that is operated by a switch or button on the handhold.

The at least one bellows or the at least one electrical pump is preferably integrated into the support, and the electronic module of the sensor instrument is preferably also integrated into the support, such that the sensor instrument is provided by the support, the modules integrated into the support, and the elements attached to the support, which in the simplest case are provided by the suction elements and the electrodes.

The electronic module is advantageously integrated into the support such that, given a successful attachment to a body of a patient, an optimally large clearance is provided between the body of the patient and the electronic module. In the case of an arc-shaped support, the electronic module is thus placed approximately in the middle of the arc. In this way, a sensor instrument is realized that can also be used together with a computed tomography apparatus, for example. The embodiment of the sensor instrument is chosen such that those components or modules of the sensor instrument that have an interfering influence on the image data generation by computed tomography apparatus could, after positioning the sensor instrument has taken place, be positioned as far distant as possible from the position that should be examined by the computed tomography apparatus. In this way, disruptions or artifacts in the relevant image region or in the relevant image content can be reduced or avoided. Interfering influences on the diagnostically relevant image portion are thus kept as far away as possible.

Furthermore, the electronic module of the sensor instrument is preferably of simple design and, in addition to signal preparation electronics, has transmission electronics for wireless transmission of the signals acquired via measurement to a receiver station. The processing and evaluation then preferably takes place outside of the sensor instrument in an apparatus at the receiver station, which for this purpose typically has a display (in addition to corresponding evaluation electronics) in order to display the prepared and/or evaluated information to the respective operator, in particular to the attending physician.

The data transmitted wirelessly are preferably prepared before transmission in the signal preparation electronics of the sensor instrument signals, that these such prepared can be fed via the wireless transmission directly into a corresponding reception unit in a computed tomography apparatus in order to then use these signals within the scope of cardiac computed tomography, for example for timing or triggering the computed tomography imaging.

In an embodiment, an integrated circuit (IC) with integrated filter stages and an analog/digital conversion circuit is used for the signal preparation electronics. This integrated circuit is connected via a digital bus to a controller or what is known as a field programmable gate array (FPGA) for conversion to the provided transmission protocol for the radio transmission, as well as signal processing steps that may possibly additionally be necessary.

Supply of the electronic module of the sensor instrument with electrical power advantageously takes place via a power storage (such as an accumulator or a capacitor) situated in the region of the electronic module. This power storage is preferably charged by inductive and/or capacitive coupling, wherein a type of charging station is preferably used for this purpose.

The wireless transmission or transfer of the data from the sensor instrument to the respective receiver station or the respective receiver preferably takes place via a simple infrared interface or an established method such as Bluetooth or ZigBee. If the transmitted data should be used for timing operation of a computed tomography apparatus, the measurement data are additionally provided with a timestamp in the sensor instrument, thus are transmitted together with a clock signal or trigger signal. In order to allow corresponding trigger applications in a computed tomography apparatus, particular attention must be paid to a low latency of the wireless connection. It is additionally advantageous to provide a data transfer protocol with error detection mechanisms and/or correction mechanisms so that an interference with the radio connection can be detected promptly, and disruptions of short duration do not lead to a functional disruption.

Methods are particularly advantageous that provide what is known as forward error correction, since these avoid the development of increased latency due to possibly required repetitions of the data transmission. Suitable forward error corrections are known and are used in diverse wireless standards. The known technique of a retransmission is typically also employed. An advantageous relationship is sought between the data redundancy that is necessary for the forward error correction (which data redundancy reduces the usable available data rate) and the number of retransmissions that are required. As the number of retransmissions increase, the latency increases and the usable data rate decreases. Since in the case of the sensor instrument disclosed herein the usable data rate is typically relatively low, but the latency should necessarily be kept low, a somewhat different compromise than in the standard use case is preferably selected for the sensor instrument according to the invention. The requirements of the sensor instrument are most comparable to requirements for video or audio transmissions, but with even greater requirements for a low latency. As a result, a procedure is preferably selected in which the number of retransmissions dictated by the underlying wireless standard is preferably minimized as much as possible, and lost data packets are accepted in order to minimize the latency. Therefore, an additional forward error correction that can deal with the lost data packets is implemented at the application protocol layer. Alternatively, one of the known wireless standards (for example Bluetooth) can be modified and optimized for the application described herein.

Furthermore, it is advantageous to integrate the electrodes of the sensor instrument into the suction elements, since handling is thereby additionally simplified. The positioning and attachment of the electrodes then takes place by the positioning and attachment of the suction elements, and no longer needs to be provided separately. A notable time saving is also achieved, which is decisive precisely in the field of emergency medicine. Depending on the application region, either contact electrodes that are designed for direct contact with the body of the respective patient or electrodes for a capacitive measurement without direct contact with the body of the respective patient are thereby used. It is additionally advantageous to integrate exactly one electrode into each suction element so that the number of electrodes corresponds to the number of suction elements.

Moreover, an embodiment is preferred in which a membrane is positioned between each suction element and the electrode integrated into it. With the use of such a membrane a chamber that can be accessed relatively well and can be cleaned easily is achieved, that rests directly on the body of a respective patient during use of the sensor instrument, and in which the negative pressure that is necessary for affixing the suction element is generated. The membrane seals off the chamber and protects the region or space of the suction element that lies behind it from contamination.

Moreover, the suction elements and/or the membranes of the sensor instrument are preferably produced from an elastic and flexible material, for example from an elastomer or silicone. In an embodiment, the elastic or flexible elements of the sensor instrument can be exchanged or even fashioned as disposable (single-use) articles, thus to be exchanged after each use of the sensor instrument.

According to a further embodiment, the suction elements are designed to be conductive at least in part and themselves serve as electrodes so that separate electrodes (in particular contact electrodes) can be foregone. The conductive design is realized by a metal coating, for example, and in this case the suction elements are preferably coated with a suitable metal coating (or at least a conductive coating) only in the immediate contact region, thus in the region that is in contact with the body of the respective patient during use.

For most use cases, the sensor instrument has electrodes with a metallic surface so that the body of the respective patient is in contact with a metal (at least in the case of contact electrodes), so a very strong impedance jump is present in the contact region between the body of the respective patient and the electrodes. However, in some cases it is advantageous to achieve essentially a weaker impedance jump by the interposition of an intermediate layer made of a material with a transition impedance, such that the impedance essentially changes in two stages, first from the impedance of the body of the respective patient to the impedance of the transition material, and then from the impedance of the transition material to the impedance of the electrode. An electrolyte is normally used as such a transition material. Suitable electrolytes can be attached to the electrodes with the use of gel pads, wherein the use of exchangeable gel pads—and in particular disposable gel pads—is preferred. Moreover, a transition from an electron conductor to an ion conductor is achieved by the use of suitable electrolytes.

DESCRIPTION OF THE PREFERRED EMBODIMENTS

Figure 1:
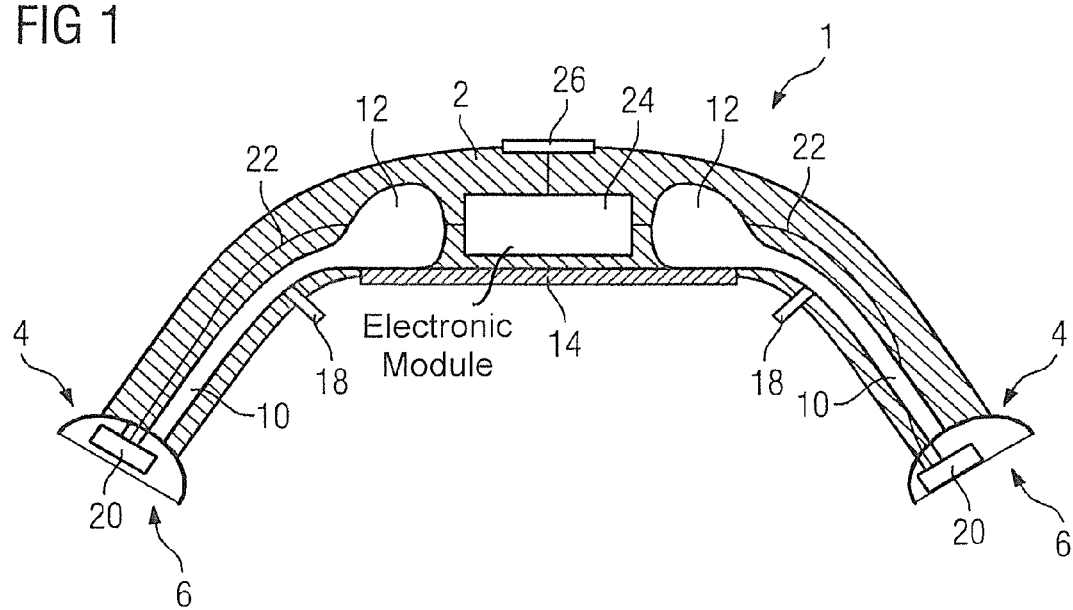
FIG. 1 shows a first embodiment of a sensor instrument in accordance with the invention, in section.
Figure 2:
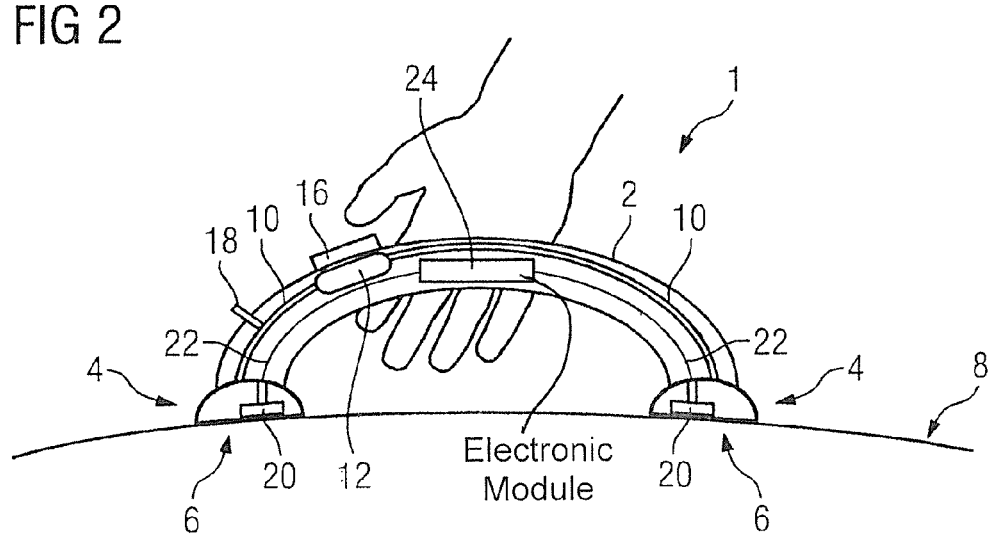
FIG. 2 shows a second embodiment of a sensor instrument in accordance with the invention.

A sensor instrument 1 as described in the following examples serves to generate electrocardiograms and—as indicated in FIG. 1 and FIG. 2—has a housing as a support 2. This housing is designed in the manner of an arc-shaped or U-shaped handhold or bow with two ends 4. A suction cup 6 as a suction element is positioned and attached to each end 4 of the support 2. Each suction cup 6 can be affixed to a body 8 of a patient by negative pressure, so as to be detachable from the body 8.

In the embodiment according to FIG. 1, each suction cup 6 is connected in a fluid-conducting manner via a connection channel 10 with a simple bellows 12 that is integrated into the support. To activate each suction cup 6—thus to generate a negative pressure within the space enclosed by the respective suction cup 6 and the body 8 of the respective patient—the associated bellows 12 is contracted. For this purpose, a pressure plate 14 positioned on the underside of the support 2 is actuated. The pressure plate 14 is thereby designed as a rigid body and, upon actuation, acts simultaneously on both bellows 12 in the support 12 so that both suction cups 12 are also simultaneously affixed to the body 8 of the respective patient.

In the embodiment shown in FIG. 2, the sensor instrument 1 has only one bellows 12, and the two suction cups 6 are each connected in a fluid-conductive manner with this bellows 12 via a connection channel 10. To activate both suction cups 6, this one bellows 12 is then contracted in that a button-like switch 16 that is positioned on the top side of the support 2 is depressed.

In both cases, this simple and purely mechanically executed system and the ergonomic embodiment of the support 2 that resembles a handhold allow a simple and one-handed handling of the sensor instrument 1. As indicated in FIG. 2, the support 2 (and thus the sensor instrument 1) is hereby gripped with one hand, approximately in the middle between the two ends 4, and is positioned on the body 8 of the respective patient. In the case of the exemplary embodiment according to FIG. 1, the affixing to the body 8 of the respective patient with the use of the suction cups 6 then takes place by an increase of the pressure exerted by hand upon gripping, so the pressure plate 14 compresses the two bellows 12. In contrast to this, in the case of the embodiment variant according to FIG. 2, the affixing of the sensor instrument 1 takes place by an actuation of the button 16, which is positioned somewhat outside of the middle region between the two ends 4 of the support 2, such that this can be comfortably reached with the thumb while the remaining fingers continue to guide the support 2, and therefore hold it in position.

In order to release the support 2 (and thus the sensor instrument 1) again from the body 8 of the respective patient, in both embodiment variants the sensor instrument 1 has at least one valve 18 via which the negative pressure (with which 1 is held to the body 8 of the respective patient) can be released again by actuation.

For detection of the electrical activities of the heart muscle fibers of patients by measurement technology, the sensor instrument 1 has two contact electrodes 20 that are integrated into the suction cups 6. In the embodiments shown in FIG. 1 and FIG. 2, the contact electrodes 20 are designed similar to a stamp and are positioned within the suction cups 6. The placement of the contact electrodes 20 hereby takes place as a result of the placement of the suction cups 6 on the body 8 of the respective patient, and after affixing of the suction cups 6 has occurred, the contact electrodes 20 rest on the body 8 so that the two contact electrodes 20 are spatially separated from one another and in direct contact with the body 8.

Via signal lines 22, the contact electrodes 20 made of metal are connected in terms of signaling with an electronic module 24, in which are contained the measurement electronics required for the detection of the electrical activities of the heart muscle fibers of patients. In addition, the electronic module 24 includes functional units (in particular an amplifier circuit) to prepare the measurement signals representing the electrical activities and a functional unit for wireless transmission of the prepared measurement signals to a receiver. Moreover, an accumulator is integrated into the electronic module 24, in order to supply the electronic module 24 with electrical power. The accumulator is designed in order to be charged by an inductive coupling at a charging station (not depicted).

In the exemplary embodiment according to FIG. 1, the electronic module additionally has a logic unit to generate display data that are then presented by a display 26. This display 26 serves as a type of monitoring display, and indicates the charge state of the accumulator, as well as the correct contacting of the contact electrodes 20 (thus whether these are in contact with the body 8 of the respective patient or not). For example, the correct contacting is determined by an impedance measurement between the contact electrodes 20 and an evaluation of the determined measurement value.

As can be seen from FIG. 1 and FIG. 2, the electronic module 24 is positioned approximately at the middle of the arc-shaped support 2 and is integrated into the support 2. The sensor instrument 1 is also suitable for use together with a computed tomography apparatus, since the electronic module 24 is positioned sufficiently distant from the body 8 of the respective patient so that image artifacts that are possibly caused by the electronic module 24 are not caused in the regions that are of interest to a medical professional and that should be detected by imaging by the computed tomography apparatus.

In the event the sensor instrument 1 is used together with a computed tomography apparatus, it is preferable to couple the sensor instrument 1 directly to the computed tomography apparatus in terms of data transfer (thus the transfer of the prepared measurement data) in order to trigger the computed tomography apparatus (for example in the case of cardiac computed tomography) with the measurement data generated by the sensor instrument 1. In this case, a corresponding receiver station or a corresponding receiver is provided for the wireless transmission of the prepared measurement data in the computed tomography apparatus.

However, the wireless transmission of the prepared measurement data is normally not predetermined for a specific receiver (and accordingly addressed to a specific receiver). Instead, multiple receivers can be used in parallel. For example, an external display device with a corresponding receiver station can be used, with the external display device designed to display an electrocardiogram on the basis of the transmitted, prepared measurement data so that a medical profession or medical technology assistant can review and monitor the cardiac function of a patient, and in fact both before starting up the computed tomography apparatus and during the creation of a computed tomography image.

It is necessary to consider that, for triggering a computed tomography acquisition via a sensor instrument provided herein, it is important that the heart activity of the patient to be examined has certain characteristics. For example, the heart rate may not be too high, and the cardiac function may not have any irregularities at all. If this is not satisfied, either the administration of medicines takes place (in particular to lower the heart rate) or the computed tomography acquisition is entirely precluded, wherein in this case an alternative examination method is applied. It is advantageous to determine and detect necessary adjustments in the examination plan promptly, thus preferably already before the patient to be examined is placed on the patient bed of the computed tomography apparatus. For example, in this context the sensor instrument disclosed herein that is designed for wireless transmission of the prepared measurement data can be used in order to determine and monitor the heart function of the patient to be examined already while he or she is in the waiting room, before the patient is directed into the computed tomography examination room. The radio transmission preferably takes place via a wireless standard that is also supported by commercially available smartphones or tablets, for example WLAN or Bluetooth. The absence of cables has the additional advantage that there is no danger that the position of the sensor instrument is altered by getting caught on a cable upon transport of the patient, for example from the waiting room into the computed tomography examination room.

Figure 3:
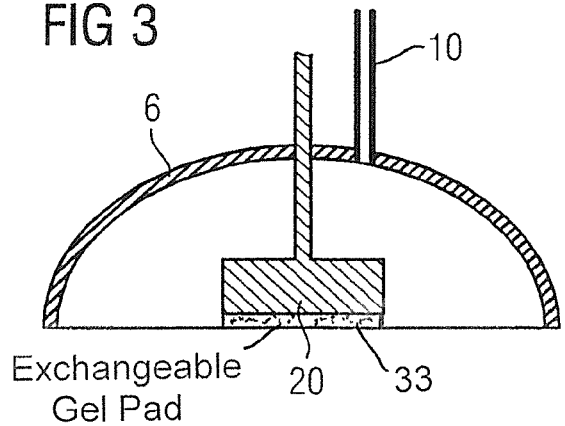
FIG. 3 shows a first of embodiment of a suction element with integrated electrode in accordance with the invention.

Furthermore, two alternative variants are respectively provided for the exemplary embodiments of the sensor instrument 2 that are shown in FIG. 1 and FIG. 2, which alternative variants differ from the exemplary embodiments in FIG. 1 and FIG. 2 primarily with regard to the embodiment of the suction cups 6 and/or the contact electrodes 20. For comparison, in FIG. 3 a suction cup 6 with integrated contact electrodes 20 is drawn as it is used in the embodiment variants presented in FIG. 1 and FIG. 2. Here a stamp-shaped contact electrode 20 is positioned within the suction cup 6. FIG. 3 also shows that an exchangeable gel pad 33 can be attached to the electrode 20.

Figure 4:
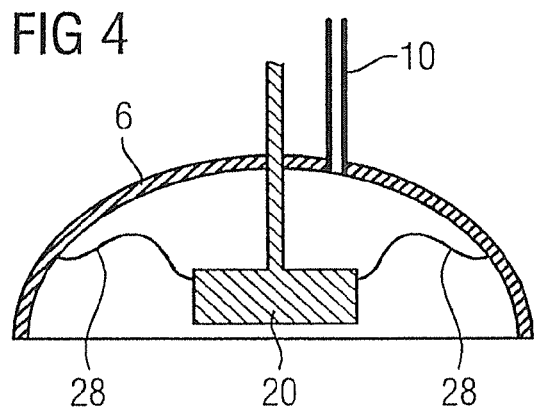
FIG. 4 shows a second embodiment of a suction element with integrated electrode in accordance with the invention.

In the embodiment according to FIG. 4, a flexible membrane 28 is inserted between the (likewise stamp-shaped) contact electrode 20 and the suction cup 6. This membrane 28 divides the spatial region encompassed by the suction cup 6 into two sub-regions and seals these sub-regions gas-tight from one another. This prevents pathogens from penetrating into the connection channels 10, and therefore transmission of illnesses between patients can be better avoided. A significant advantage of this embodiment is that the instrument can be more easily cleaned and disinfected.

Figure 5:
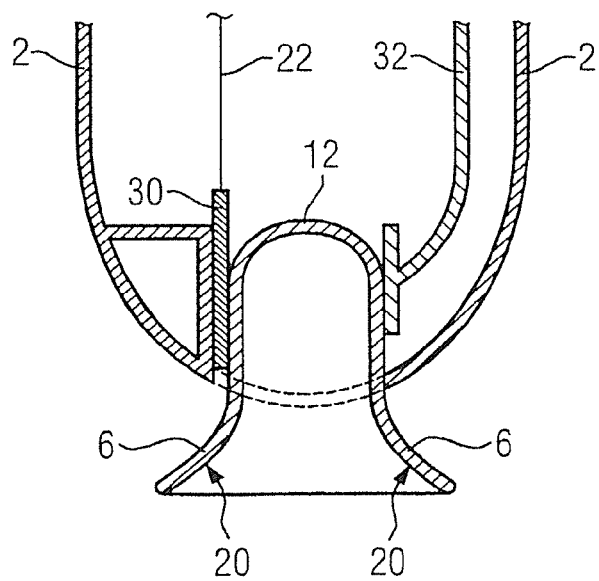
FIG. 5 shows a third embodiment of a suction element with integrated electrode in accordance with the invention.

A further embodiment variant is schematically depicted in FIG. 5. Here the suction cup 6 itself is executed so as to be conductive via a metallization (such as a vapor-deposited metal layer) so that an additional, separate contact electrode 20 within the suction cup 6 can be omitted. Here the suction cup 6 itself acts as a contact electrode 20, and accordingly is connected with the electronic module 24 via a contacting 30 and a signal line 22 connected thereto.

Figure 6:
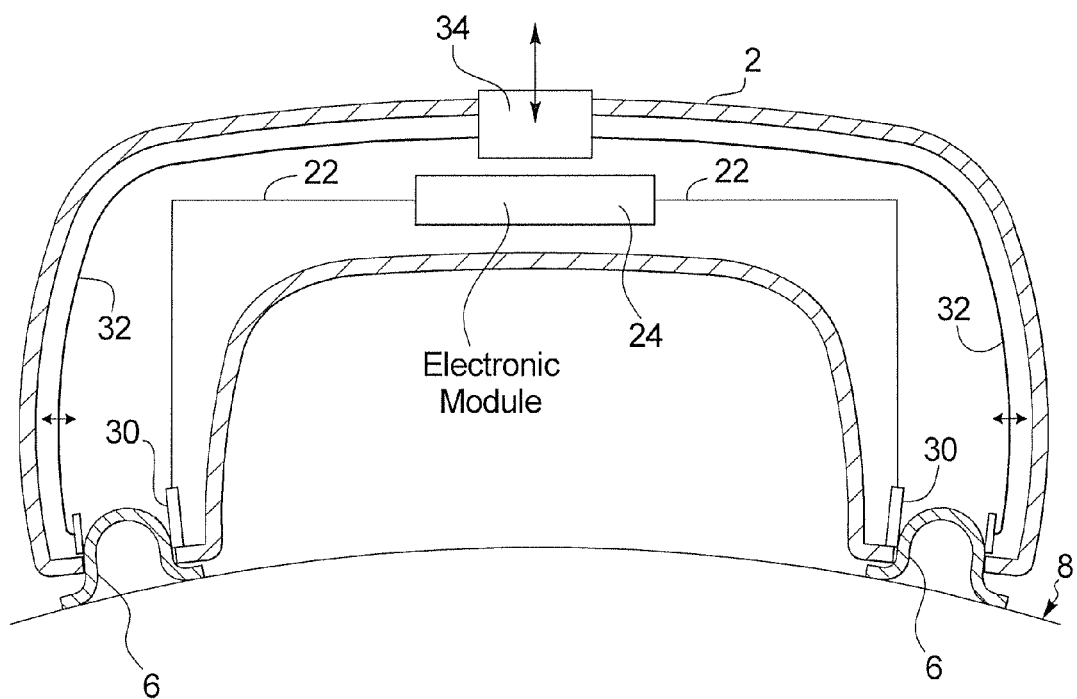
FIG. 6 shows how the suction elements in the third embodiment of FIG. 5 are actuated.

In addition, FIG. 5 shows an embodiment variant of the sensor instrument 1 in which a separate bellows 12 and a connection channel 10 can be omitted. In this embodiment, the suction cup 6 also takes on the function of the bellows 12, and accordingly the suction cup 6 contracts to activate the suction cup 6 in response to a lever 32 within the support 2 being pressed against a wall of the suction cup 6. This lever 32 is activated by a button 34 that is positioned at a point that is most advantageous for gripping, as shown in FIG. 6. In an alternative embodiment, instead of the lever 32, a Bowden cable is used.

Although modifications and changes may be suggested by those skilled in the art, it is the intention of the inventors to embody within the patent warranted hereon all changes and modifications as reasonably and properly come within the scope of their contribution to the art.

We claim as our invention:

1. A sensor instrument for extracorporeally detecting electrical signals representing electrical activity of cardiac muscle fibers of a subject, comprising:
   a support having two free ends;
   two electrodes;
   said support having two suction elements respectively at said free ends that are operable to extracorporeally affix said free ends of said support to a body surface of a subject, said two suction elements respectively carrying said two electrodes and, when the suction elements are extracorporeally affixed to said body surface, said suction elements causing the respective two electrodes to detect said electrical signals representing said electrical activity of cardiac muscle fibers in said subject;
   each of said two suction elements having a lever actuator adjacent thereto that, when actuated, causes the suction element adjacent thereto to become affixed to the body surface of the subject;
   a manually actuatable button connected to each of said two lever actuators that, when actuated, simultaneously actuates each of said two lever actuators to simultaneously affix each of said two suction elements to the body surface of the subject; and
   an electronic module carried by said support and electrically connected to said electrodes, said electronic module being configured to emit a module output signal corresponding to said signals detected by said electrodes.

2. A sensor arrangement as claimed in claim 1 wherein said support comprises a handhold configured for manual gripping of said support.

3. A sensor arrangement as claimed in claim 1 wherein said support itself is configured as a handhold allowing manual gripping of said support.

4. A sensor arrangement as claimed in claim 3 wherein said support is arc-shaped having two opposite ends at which said suction elements are respectively attached.

5. A sensor arrangement as claimed in claim 1 wherein said support is mechanically adjustable to allow a spacing between said suction elements to be adjusted.

6. A sensor arrangement as claimed in claim 1 wherein said electronic module is integrated into said support.

7. A sensor arrangement as claimed in claim 1 wherein said electronic module is configured to wirelessly transmit said output signal to a location remote from said support.

8. A sensor arrangement as claimed in claim 1 wherein said electrodes are integrated into said suction elements.

9. A sensor arrangement as claimed in claim 8 wherein said suction elements are electrically conductive, and form said electrodes.

10. A sensor arrangement as claimed in claim 8 wherein said suction elements each comprise a metal coating.

11. A sensor arrangement as claimed in claim 1 for extracorporeally detecting electrical signals representing electrical activity of cardiac muscle fibers of a subject, comprising:
    a support having two free ends;
    two electrodes;
    said support having two suction elements respectively at said free ends that are operable to extracorporeally affix said free ends of said support to a body surface of a subject, said two suction elements respectively carrying said two electrodes and, when the suction elements are extracorporeally affixed to said body surface, said suction elements causing the respective two electrodes to detect said electrical signals representing said electrical activity of cardiac muscle fibers in said subject;
    a bellows carried by said support, said bellows being in fluid communication with said suction elements to mechanically activate said suction elements; and
    an electronic module carried by said support and electrically connected to said electrodes, said electronic module being configured to emit a module output signal corresponding to said signals detected by said electrodes.

12. A sensor arrangement as claimed in claim 11 wherein said bellows is integrated into said support.

* * * * *